US012396978B2

(12) United States Patent
Komorisono

(10) Patent No.: US 12,396,978 B2
(45) Date of Patent: Aug. 26, 2025

(54) EXTERNAL-USE COMPOSITION

(71) Applicant: KOBAYASHI PHARMACEUTICAL CO., LTD., Osaka (JP)

(72) Inventor: Masahiko Komorisono, Ibaraki (JP)

(73) Assignee: KOBAYASHI PHARMACEUTICAL CO., LTD., Osaka (JP)

( * ) Notice: Subject to any disclaimer, the term of this patent is extended or adjusted under 35 U.S.C. 154(b) by 839 days.

(21) Appl. No.: 17/255,007

(22) PCT Filed: Jun. 19, 2019

(86) PCT No.: PCT/JP2019/024352
§ 371 (c)(1),
(2) Date: Dec. 22, 2020

(87) PCT Pub. No.: WO2020/004193
PCT Pub. Date: Jan. 2, 2020

(65) Prior Publication Data
US 2021/0244707 A1    Aug. 12, 2021

(30) Foreign Application Priority Data
Jun. 28, 2018  (JP) .................................. 2018-122790

(51) Int. Cl.
*A61K 31/375*    (2006.01)
*A61K 8/41*    (2006.01)
(Continued)

(52) U.S. Cl.
CPC .......... *A61K 31/375* (2013.01); *A61K 47/183* (2013.01); *A61K 47/26* (2013.01); *A61K 47/36* (2013.01)

(58) Field of Classification Search
CPC .... A61K 31/375; A61K 47/183; A61K 47/26; A61K 47/36; A61K 9/0014; A61K 8/41;
(Continued)

(56) References Cited

U.S. PATENT DOCUMENTS

2006/0134095 A1*  6/2006  Ito ............................. A61K 8/19
424/125
2007/0232687 A1* 10/2007  Kato ...................... A61K 8/678
514/458

(Continued)

FOREIGN PATENT DOCUMENTS

CN    104994849 A    10/2015
JP    H11199426 A    7/1999
(Continued)

OTHER PUBLICATIONS

International Search Report dated Sep. 24, 2019 for International Patent Application No. PCT/JP2019/024352, 4 pages with English translation.

*Primary Examiner* — Bethany P Barham
*Assistant Examiner* — Janet Joseph
(74) *Attorney, Agent, or Firm* — MH2 Technology Law Group, LLP

(57) ABSTRACT

A composition for external use comprising (A) an ascorbic acid compound, derivatives and salts thereof; (B) an edetic acid salt; (C) a glycyrrhizic acid salt; (D) a heparinoid; and (E) water and an ascorbic acid compound-containing composition for external use in which precipitation under low-temperature storage conditions is suppressed.

4 Claims, 1 Drawing Sheet

(A) Initial (before storage)

(B) After storage at 5°C for 2 days

(51) Int. Cl.

| | |
|---|---|
| *A61K 8/44* | (2006.01) |
| *A61K 8/63* | (2006.01) |
| *A61K 8/67* | (2006.01) |
| *A61K 8/73* | (2006.01) |
| *A61K 9/06* | (2006.01) |
| *A61K 9/08* | (2006.01) |
| *A61K 47/18* | (2017.01) |
| *A61K 47/26* | (2006.01) |
| *A61K 47/36* | (2006.01) |
| *A61P 17/00* | (2006.01) |
| *A61P 17/02* | (2006.01) |
| *A61P 17/16* | (2006.01) |
| *A61Q 19/00* | (2006.01) |
| *A61Q 19/02* | (2006.01) |

(58) Field of Classification Search
CPC ... A61K 8/44; A61K 8/63; A61K 8/67; A61K 8/73; A61K 9/06; A61K 9/08; A61P 17/00; A61P 17/02; A61P 17/16; A61Q 19/00; A61Q 19/02
See application file for complete search history.

(56) References Cited

U.S. PATENT DOCUMENTS

| | | | | |
|---|---|---|---|---|
| 2008/0153757 | A1* | 6/2008 | Beeson | A61Q 19/08 |
| | | | | 514/474 |
| 2010/0209364 | A1* | 8/2010 | Abe | A61K 8/31 |
| | | | | 424/59 |
| 2016/0015619 | A1 | 1/2016 | Lee | |

FOREIGN PATENT DOCUMENTS

| | | | | |
|---|---|---|---|---|
| JP | 2000-53533 | A | 2/2000 | |
| JP | 2003-113061 | A | 4/2003 | |
| JP | 2012-36183 | A | 2/2012 | |
| JP | 5876962 | B2 * | 3/2016 | ............. A61K 31/05 |
| JP | 2016-130224 | A | 7/2016 | |
| JP | 5961034 | B2 * | 8/2016 | |
| JP | 2016-179958 | A | 10/2016 | |
| JP | 2017-48163 | A | 3/2017 | |
| WO | 2009127058 | A1 | 10/2009 | |
| WO | WO-2016013551 | A1 * | 1/2016 | ............. A61K 31/19 |
| WO | 2016/159186 | A1 | 10/2016 | |

* cited by examiner (A) Initial (before storage)
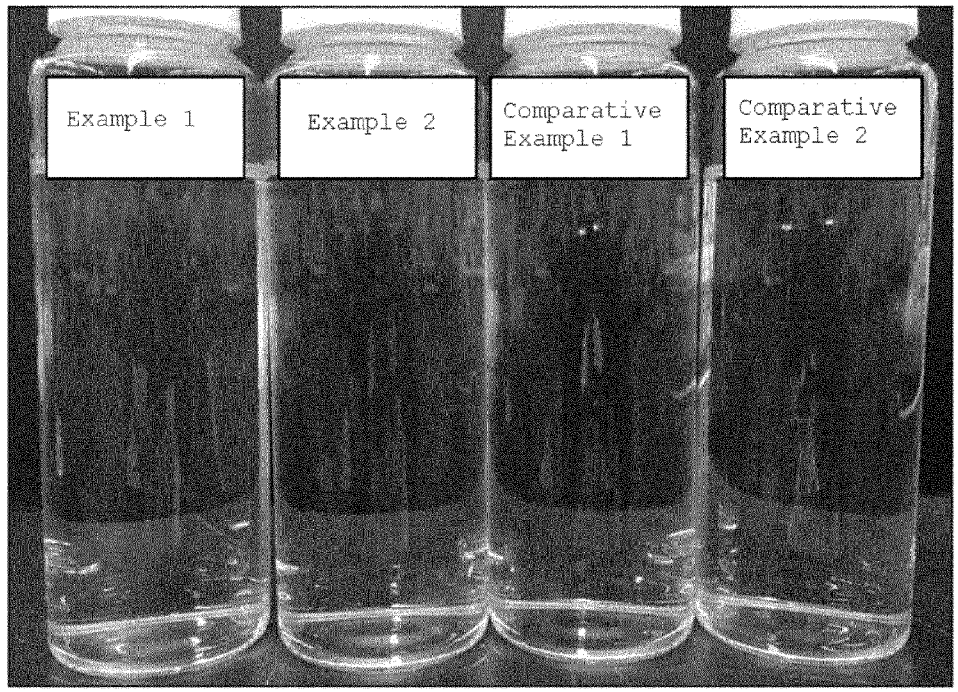
(B) After storage at 5°C for 2 days
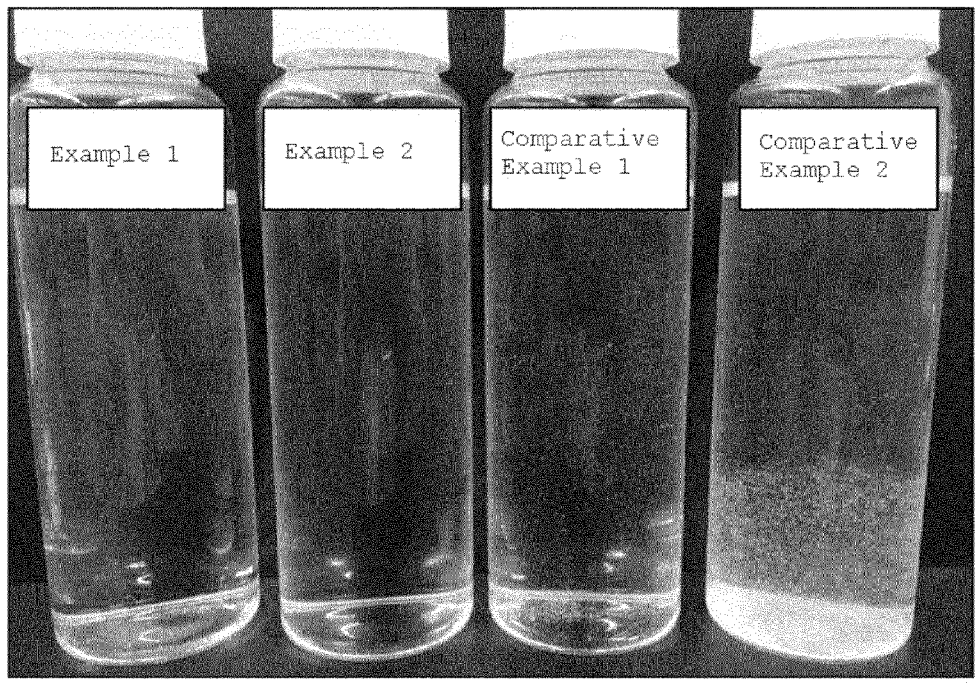

EXTERNAL-USE COMPOSITION

CROSS-REFERENCE TO RELATED APPLICATIONS

This application is a U.S. National Stage application of PCT/JP2019/024352, filed 19 Jun. 2019, which claims priority to Japanese Application No. 2018-122790, filed 28 Jun. 2018, the entire disclosures of which are incorporated herein by reference in their entireties.

TECHNICAL FIELD

The present invention relates to a composition for external use, comprising an ascorbic acid compound. More preferably, the present invention relates to an ascorbic acid compound-containing composition for external use, in which precipitation under a low-temperature storage condition is suppressed. The present invention also relates to a method for suppressing precipitation in an ascorbic acid compound-containing composition for external use, under a low-temperature storage condition.

BACKGROUND ART

Ascorbic acid or salts thereof have been used as antioxidants (oxidation inhibitors) to prevent the oxidation of products themselves due to their strong antioxidant action; and have been also widely used in cosmetics, pharmaceutical products for external use, or quasi-drugs for external use due to their antioxidant action-based melanin production suppression action (whitening action). Moreover, many ascorbic acid derivatives with enhanced penetration into skin have been developed.

It is known that although these ascorbic acid compounds have relatively high solubility in water, they are difficult to dissolve in lower alcohols such as ethanol, and further exhibit poorer solubility in polyhydric alcohols such as glycerol. Thus, ascorbic acid compounds have the problem such that their solubility decreases depending on the solvent and components mixed therewith; and tend to precipitate, in particular, under a low-temperature condition. However, to the Applicant's knowledge, the problem of precipitation in an aqueous composition containing an ascorbic acid compound, or an improvement method for precipitation, has not yet been proposed.

SUMMARY OF INVENTION

Technical Problem

The inventor found, during daily research, that a composition for external use in which ascorbic acid is dissolved in water together with an edetic acid salt and a glycyrrhizic acid salt shows precipitation of white crystals in storage for as short a period as 2 days at a low temperature of 5° C., and thus has poor storage stability. Such a phenomenon also occurs when an ascorbic acid derivative is used in place of ascorbic acid.

An object of the present invention is to suppress precipitation in a composition for external use in which ascorbic acid, a derivative thereof, or a salt thereof (which may be referred to as an "ascorbic acid compound" in the present specification) is dissolved in water together with an edetic acid salt and a glycyrrhizic acid salt, to improve storage stability. Specifically, an object of the present invention is to provide a composition for external use that has good storage stability with suppressed precipitation under a low-temperature condition while containing an ascorbic acid compound, an edetic acid salt, a glycyrrhizic acid salt, and water.

Solution to Problem

The inventor conducted extensive research to achieve the above objects. The inventor found that precipitation under a low-temperature condition is significantly suppressed, and storage stability is improved, by incorporating a heparinoid in addition to an ascorbic acid compound, an edetic acid salt, a glycyrrhizic acid salt, and water.

The present invention has been accomplished based on this finding, and includes the following embodiments.

(I) Composition for External Use (I-1) A composition for external use, comprising the following components (A) to (E):
- (A) at least one member selected from the group consisting of ascorbic acid, derivatives thereof, and salts thereof;
- (B) an edetic acid salt;
- (C) a glycyrrhizic acid salt;
- (D) a heparinoid; and
- (E) water.

(I-2) The composition for external use according to (I-1), wherein component (A) is present in a total amount of 0.01 to 10 mass %, based on the composition for external use taken as 100 mass %.

(I-3) The composition for external use according to (I-1) or (I-2), wherein component (D) is present in a total amount of 0.5 to 500 parts by mass relative to 100 parts by mass of component (A) in the composition for external use.

(I-4) The composition for external use according to any one of (I-1) to (I-3), which has a pH in the range of 3 to 7.

(I-5) The composition for external use according to any one of (I-1) to (I-4), which is a liquid or semi-solid composition.

(I-6) The composition for external use according to any one of (I-1) to (I-5), which is a cosmetic, a pharmaceutical product for external use, or a quasi-drug for external use.

(I-7) The composition for external use according to any one of (I-1) to (I-6), which is a composition in which crystal precipitation in storage at 5° C. is suppressed.

(II) Method for Suppressing Precipitate Formation (II-1) A method for suppressing precipitate formation in a composition for external use comprising the following components (A), (B), (C), and (E), the method comprising mixing the following components (A) to (E) to allow components (A), (B), (C), and (E) to coexist with component (D):
- (A) at least one member selected from the group consisting of ascorbic acid, derivatives thereof, and salts thereof;
- (B) an edetic acid salt;
- (C) a glycyrrhizic acid salt;
- (D) a heparinoid; and
- (E) water.

(II-2) The method for suppressing precipitate formation according to (II-1), wherein the composition for external use comprises component (A) in a total amount of 0.01 to 10 mass %.

(II-3) The method for suppressing precipitate formation according to (II-1) or (II-2), wherein component (D) is incorporated in a total amount of 0.5 to 500 parts by mass relative to 100 parts by mass of component (A) in the composition for external use.

(II-4) The method for suppressing precipitate formation according to any one of (II-1) to (II-3), comprising adjusting the pH of the composition for external use to 3 to 7.

(II-5) The method for suppressing precipitate formation according to any one of (II-1) to (II-4), wherein the composition is a liquid or semi-solid composition.

(II-6) The method for suppressing precipitate formation according to any one of (II-1) to (II-5), wherein the composition is a cosmetic, a pharmaceutical product for external use, or a quasi-drug for external use.

(II-7) The method for suppressing precipitate formation according to any one of (II-1) to (II-6), wherein the method is a method for suppressing crystal precipitation in storage at 5° C.

Advantageous Effects of Invention

According to the present invention, the formation of precipitates under a low-temperature condition can be suppressed in a composition for external use comprising an ascorbic acid compound, an edetic acid salt, a glycyrrhizic acid salt, and water. Thus, according to the present invention, an ascorbic acid compound-containing composition with improved or enhanced storage stability at low temperature can be provided.

BRIEF DESCRIPTION OF DRAWINGS

FIG. 1 shows the results of Experimental Example 1. (A) is an image of the appearance of test samples (Examples 1 to 2 and Comparative Examples 1 to 2) immediately after preparation (before low-temperature storage). (B) is an image of the appearance of the test samples (Examples 1 to 2 and Comparative Examples 1 to 2) after low-temperature storage (5° C., 2 days).

DESCRIPTION OF EMBODIMENTS (I) Composition for External Use

The composition for external use of the present invention comprises components (A) to (E) described below.

Component (A): Ascorbic Acid Compound (a) Ascorbic Acid

The ascorbic acid used in the present invention is not particularly limited as long as it is used, in particular, as a component of an external preparation in the field of cosmetics, pharmaceutical products, or quasi-drugs. Preferable examples include L-ascorbic acid, which is known by the trivial name of vitamin C.

(b) Derivatives of Ascorbic Acid

The derivatives of ascorbic acid are not limited as in ascorbic acid as long as they are used as a component of an external preparation that is a cosmetic, a pharmaceutical product, or a quasi-drug. Preferable examples include, but are not limited to, ester derivatives and ether derivatives. Specific examples of ester derivatives of ascorbic acid include phosphoric acid esters of ascorbic acid, such as L-ascorbic acid monophosphate, L-ascorbic acid diphosphate, and L-ascorbic acid triphosphate; fatty acid esters of ascorbic acid, such as L-ascorbic acid palmitate, L-ascorbic acid isopalmitate, L-ascorbic acid stearate, and L-ascorbic acid isostearate; L-ascorbic acid-2-sulfate; and the like. Specific examples of ether derivatives of ascorbic acid include alkyl ethers of ascorbic acid, such as L-ascorbic acid methyl ether, L-ascorbic acid ethyl ether, L-ascorbic acid propyl ether, and L-ascorbic acid butyl ether; glucosides of ascorbic acid, such as L-ascorbic acid-2-glucoside; and the like. Water-soluble or highly water-soluble ester derivatives or ether derivatives are preferable. Examples of the water-soluble or highly water-soluble ester derivatives or ether derivatives include ester derivatives such as the phosphoric acid esters of ascorbic acid described above and L-ascorbic acid-2-sulfate; and ether derivatives such as L-ascorbic acid ethyl ether and L-ascorbic acid-2-glucoside.

(c) Salts of Ascorbic Acid or Derivatives Thereof

Examples of salts of ascorbic acid or derivatives thereof include salts of alkali metals such as sodium and potassium; salts of alkaline earth metals such as magnesium, calcium, and barium; metal salts including salts of multivalent metals such as aluminum; ammonium salts such as salts of ammonium and tricyclohexyl ammonium; and salts of alkanolamines such as monoethanolamine, diethanolamine, triethanolamine, monoisopropanolamine, diisopropanolamine, and triisopropanolamine. Salts of alkali metals such as sodium are preferable.

Preferable examples of the ascorbic acid compound include L-ascorbic acid, L-ascorbic acid phosphoric acid esters, L-ascorbic acid-2-sulfate, L-ascorbic acid-2-glucoside, ascorbic acid ethyl ether, and salts thereof. L-ascorbic acid, L-ascorbic acid monophosphate, L-ascorbic acid-2-glucoside, ascorbic acid ethyl ether, and salts thereof are particularly preferable in terms of their high safety and effect on the skin or mucous membrane when used as a component of a composition for external use.

The content of the ascorbic acid compound in the composition for external use of the present invention can be selected from the range of 0.01 to 10 mass %, based on the total amount of the composition for external use taken as 100 mass %. In terms of exerting antioxidation action, the ascorbic acid compound is preferably present in an amount of about 0.01 mass % or more. In terms of exerting melanin production suppression action, the ascorbic acid compound is preferably present in an amount of about 3 mass % or more. To suitably achieve the precipitation suppression effect obtained by incorporating heparin or a substance similar to heparin described later, the content of the ascorbic acid compound may be, for example, about 0.1 mass % or more, preferably 0.3 to 10 mass %, and more preferably 1 to 5 mass %.

Component (B): Edetic Acid Salt

The edetic acid salt is not limited as long as it is a pharmaceutically acceptable salt and is used as a component of an external preparation that is a cosmetic, a pharmaceutical product, or a quasi-drug. Examples include, but are not limited to, salts of alkali metals such as sodium and potassium; salts of alkaline earth metals such as magnesium, calcium, and barium; metal salts including salts of multivalent metals such as aluminum; and ammonium salts such as salts of ammonium and tricyclohexyl ammonium. Preferable examples include alkali metal salts such as disodium edetate and tetrasodium edetate; alkaline earth metal salts such as calcium disodium edetate; and the like. Disodium edetate is preferable. These edetic acid salts also encompass hydrates (hydrate salt) such as tetrasodium edetate tetrahydrate. The edetic acid salt is preferably disodium edetate. Disodium edetate, also referred to as sodium edetate, sodium ethylenediaminetetraacetate, or sodium EDTA, has been widely used as a stabilizing agent, a sequestering agent, an antioxidant, an antimicrobial agent, an antiseptic, or a preservative in the field of cosmetics, pharmaceutical products, or quasi-drugs.

The content of the edetic acid salt in the composition for external use of the present invention can be selected and set from the range in which it is acceptable to incorporate the edetic acid salt into an external preparation that is a cosmetic, a pharmaceutical product, or a quasi-drug. Although there is no limitation thereto, the content of the edetic acid salt can be selected from the range of, for example, 0.01 to 0.5 mass %; and is preferably 0.01 to 0.3 mass %, and more preferably 0.05 to 0.2 mass %.

Component (C): Glycyrrhizic Acid Salt

In the same manner as the edetic acid salt, the glycyrrhizic acid salt is not limited as long as it is a pharmaceutically acceptable salt and is used as a component of an external preparation that is a cosmetic, a pharmaceutical product, or a quasi-drug. Examples include, but are not limited to, salts of alkali metals such as sodium and potassium; salts of alkaline earth metals such as magnesium, calcium, and barium; metal salts including salts of multivalent metals such as aluminum; and ammonium salts such as salts of ammonium and tricyclohexyl ammonium. Preferable examples include alkali metal salts such as disodium glycyrrhizinate, trisodium glycyrrhizinate, and dipotassium glycyrrhizinate; and ammonium salts such as monoammonium glycyrrhizinate and diammonium glycyrrhizinate. Dipotassium glycyrrhizinate is preferable. These glycyrrhizic acid salts have been widely used as antiphlogistic agents (anti-inflammatory agents), flavoring agents, and skin conditioning agents in the field of external preparations that are cosmetics, pharmaceutical products, or quasi-drugs.

The content of the glycyrrhizic acid salt in the composition for external use of the present invention can be selected and set from the range in which it is acceptable to incorporate the glycyrrhizic acid salt into an external preparation that is a cosmetic, a pharmaceutical product, or a quasi-drug. Although there is no limitation thereto, the content of the glycyrrhizic acid salt can be selected from the range of, for example, 0.001 to 5 mass %; and is preferably 0.01 to 3 mass %, and more preferably 0.05 to 2 mass %.

Component (D): Heparinoid

The heparinoid, which is a component conventionally known to have, for example, blood circulation promotion action and skin moisturizing action, is a polysulfated mucopolysaccharide, such as chondroitin polysulfate. It is preferable that the heparinoid contains an average of 0.5 to 5 sulfate groups, particularly an average of 0.6 to 3 sulfate groups, per monosaccharide molecule that constitutes the mucopolysaccharide. The heparinoid also encompasses, for example, heparin; chondroitin polysulfate such as chondroitin sulfate D and chondroitin sulfate E; and the like. In particular, a heparinoid (Hirudoid) listed in the Japanese Pharmaceutical Codex can be suitably used.

The content of the heparinoid in the composition for external use of the present invention can be selected and set from the range in which it is acceptable to incorporate the heparinoid into an external preparation that is a cosmetic, a pharmaceutical product, or a quasi-drug. Although there is no limitation thereto, the content of the heparinoid can be selected from the range of, for example, 0.01 to 1 mass %; and is preferably 0.05 to 0.5 mass %, and more preferably 0.05 to 0.4 mass %.

Although there is no limitation thereto, the heparinoid is preferably present in an amount of 0.5 to 500 parts by mass, more preferably 1 to 50 parts by mass, and particularly preferably 3 to 20 parts by mass, relative to 100 parts by mass of the ascorbic acid compound (A) contained in the composition for external use of the present invention.

Although there is no limitation thereto, the heparinoid is preferably present in an amount of 10 to 3000 parts by mass, more preferably 30 to 1000 parts by mass, and particularly preferably 50 to 500 parts by mass, relative to 100 parts by mass of the edetic acid salt (B) contained in the composition for external use of the present invention.

Further, although there is no limitation thereto, the heparinoid is preferably present in an amount of 10 to 10000 parts by mass, more preferably 10 to 3000 parts by mass, and particularly preferably 10 to 1000 parts by mass, relative to 100 parts by mass of the glycyrrhizic acid salt (C) contained in the composition for external use of the present invention.

The proportion of the heparinoid (component (D)) relative to component (A), component (B), and/or component (C) in the above ranges improves the storage stability of an aqueous composition containing components (A), (B), (C), and (D) at low temperature, and significantly suppresses the precipitation of crystals (formation of precipitates) that can occur when component (D) is not contained.

Component (E): Water

The water is not particularly limited as long as it generally has a purity or a degree of purification that allows for use in a composition for external use (cosmetic, pharmaceutical product, or quasi-drug), depending on the use of the composition. Specifically, ion-exchanged water, distilled water, purified water, sterile water, and the like can be used without limitation. Purified water, ion-exchanged water, and sterile water can be suitably used in terms of hygiene and storage stability. The amount of water is an amount that ultimately brings the entire composition to 100 mass %. Specifically, the amount of water can be selected and adjusted within the range in which the precipitation suppressing effect of the present invention is exhibited without impairing the form of the composition for external use of the present invention. The amount of water is not limited; and may be, for example, 10 to 99.8 mass %, preferably 50 to 99 mass %, and more preferably 70 to 95 mass %.

Other Components

The composition for external use of the present invention may comprise known additives added to pharmaceutical products, quasi-drugs, or cosmetics, in amounts and qualities that do not impair the storage stability (precipitation suppression), which is an effect of the present invention; and do not impair the effect of each component contained. Examples of additives include bases, surfactants, thickeners, preservatives, oxidation inhibitors, chelating agents, stabilizers, irritation reducing agents, coloring agents, flavors, and the like. Moreover, in order to add other useful actions, the composition for external use of the present invention may comprise known active ingredients added to pharmaceutical products, quasi-drugs, or cosmetics, in amounts and qualities that do not impair the storage stability (precipitation suppression), which is an effect of the present invention; and do not impair the effect of each component contained. Examples of active ingredients include anti-inflammatory agents, moisturizing agents, vitamins, astringents, antimicrobial components, peptides or derivatives thereof, amino acids or derivatives thereof, cell activating components, antiaging components (anti-wrinkle agents), blood circulation promoting components, skin-whitening components, natural extracts, enzymes, bactericides, and the like.

pH of Composition for External Use

The pH of the composition for external use of the present invention is not limited; and is preferably adjusted to the range of 2 to 9, and more preferably 3 to 7. Adjusting the pH to the above range enables the composition of the present invention to be prepared as a more stable composition for external use. The pH may be adjusted using a pH adjuster according to an ordinary method, if necessary. Examples of pH adjusters include organic acids (e.g., citric acid, lactic acid, acetic acid, tartaric acid, malic acid, succinic acid, oxalic acid, fumaric acid, gluconic acid, and aspartic acid) and salts thereof; inorganic acids (e.g., hydrochloric acid, sulfuric acid, phosphoric acid, polyphosphoric acid, and boric acid) and salts thereof; inorganic salts (e.g., sodium hydrogencarbonate, sodium carbonate, sodium hydroxide, and potassium hydroxide); organic salts (e.g., amines such as monoethanolamine and triethanolamine); and the like.

Form

The composition for external use of the present invention may consist of components (A) to (E) described above. However, as long as the effects of the present invention are not impaired, the composition may be mixed with a base or a carrier commonly used in pharmaceutical products, quasi-drugs, or cosmetics; and, if necessary, additives and useful components, to prepare a composition for external use for pharmaceutical products, quasi-drugs, or cosmetics.

The composition for external use of the present invention is in the form of a liquid or a semi-solid. The liquid or semi-solid form means that the composition is in the form of a liquid or a semi-solid at least at a low temperature (5° C.) to ordinary temperature (25±5° C.). The term "semi-solid" means a form that flows under its own weight. Examples of those in the form of a liquid or semi-liquid include solutions, colloidal solutions (sols, suspensions, and emulsions), gels, and the like.

When the composition for external use of the present invention is a pharmaceutical product, the pharmaceutical form of the composition is not particularly limited. Examples include liquids and solutions, suspensions, emulsions, creams, ointments, gels, liniments, lotions, and the like. The pharmaceutical composition for external use is preferably used in the form of a liquid or solution, an emulsion, or a gel; and more preferably in the form of a liquid or solution, or a gel. These preparations can be produced according to, for example, the methods described in the general rules for preparations of the Japanese Pharmacopoeia, 17th edition.

When the composition for external use of the present invention is a quasi-drug or a cosmetic, the form of the composition is not particularly limited. Examples include skin care products and cosmeceuticals, such as skin lotions, emulsions, creams, serums, hand creams, and body lotions.

Production Method

The method for preparing the composition for external use of the present invention is not particularly limited. The composition for external use can be prepared according to an ordinary method based on the type and use of the composition for external use (pharmaceutical product, quasi-drug, or cosmetic), and the shape thereof. Specifically, for example, components (A) to (E) described above, or components (A) to (E) and, if necessary, ordinary components required to prepare a composition for external use, may be suitably selected and mixed to prepare the composition according to an ordinary method.

The composition for external use thus produced is filled and contained in a container. The container may have any shape, as long as it can contain a liquid or semi-solid composition. The shape of the container can be appropriately selected depending on the form, use, and method of use (administration method) of the composition. Examples of containers include, but are not limited to, bottle containers (roll-on containers, bottle containers having a sponge-like application member on the head, jar bottle containers), pump spray containers, pump discharge containers, containers for aerosols, tube containers, and the like. In the composition for external use of the present invention contained in a container, precipitation is significantly suppressed under a low-temperature condition. For example, when the composition is allowed to stand at 5° C. for 2 days, the formation of precipitates is suppressed compared with that in a composition for external use that does not contain component (D).

Method of Use and Application

The dosage regimen of the composition for external use of the present invention applied to the integument is not particularly limited. The composition for external use of the present invention can be generally used, for example, by applying it to an integument, such as the skin, in an appropriate amount several times a day. Examples of applications of the composition for external use of the present invention include, but are not particularly limited to, pharmaceutical applications (treatment and improvement), skin care applications, and the like. The composition for external use of the present invention is preferably used for the purpose of, for example, moisturizing, anti-inflammation, caring for (moisturizing) marks (scars, burn scars, acne scars, stretch marks) left on the skin to make the marks less noticeable, or preventing keloid formation.

(II) Method for Suppressing Precipitate Formation

The present invention relates to a method for suppressing formation of precipitates during low-temperature storage of a composition for external use comprising (A) at least one ascorbic acid compound, (B) an edetic acid salt, (C) a glycyrrhizic acid salt, and (E) water described above. This method can be carried out by allowing components (A) to (C) of the composition for external use to coexist with (D) a heparinoid in the presence of component (E). This coexistence state can be conveniently obtained by adding component (D) when producing a composition for external use comprising components (A) to (C) and (E). Specifically, precipitation during low-temperature storage of a composition for external use comprising components (A) to (C) and (E) can be suppressed by incorporating component (D) when producing the composition for external use comprising components (A) to (C) and (E).

The phrase "low-temperature storage" as used herein means static storage at ordinary pressure and a temperature of 5° C. for 2 days or more. The phrase "suppressing precipitate formation in low-temperature storage" means that the formation of precipitates that can occur in a composition for external use comprising (A) at least one ascorbic acid compound, (B) an edetic acid salt, (C) a glycyrrhizic acid salt, and (E) water by at least static storage at ordinary pressure and a temperature of 5° C. for 2 days or more is suppressed by using (D) a heparinoid in combination. The suppression includes not only complete inhibition (prevention) of precipitate formation, but also delay of precipitate formation. Whether the formation of precipitates is suppressed can be evaluated by allowing a composition for external use comprising (A) at least one ascorbic acid compound, (B) an edetic acid salt, (C) a glycyrrhizic acid salt, (D) a heparinoid, and (E) water (test sample) and a control sample in which (D) a heparinoid is excluded from the test sample to at least stand at ordinary pressure and a temperature of 5° C. for 2 days or more; and comparing the formation of precipitates in the two samples, as shown in Experimental Example 1 described later. When the formation of precipitates in the test sample is suppressed compared with that in the control sample, it can be determined that the method of the present invention has been carried out for the test sample. Moreover, instead of "static storage at ordinary pressure and a temperature of 5° C. for 2 days or more," an accelerated test that can be regarded as an equivalent condition can be used; and the same determination can also be made when the formation of precipitates in the test sample is suppressed compared with that in the control sample in the accelerated test.

The kinds and proportions of components (A), (B), (C), (D), and (E) used in the method of the present invention, and the composition for external use comprising these components, are as described in section (I); and the descriptions in section (I) can be incorporated herein by reference.

EXAMPLES

Examples are given below to illustrate the structure and effects of the present invention in more detail. However, these Examples are for illustrative purposes only, and the present invention is not limited to these Examples. In the Examples, "%" indicates "mass %," and "parts" indicates "parts by mass," unless otherwise noted. Unless otherwise specified, production and experiments were performed at ordinary pressure and ordinary temperature.

Experimental Example 1

Storage Stability Test

The components shown in Table 1 were weighed, stirred and mixed; and dissolved to prepare compositions in the form of an aqueous solution (Examples 1 and 2 and Comparative Examples 1 and 2). Each composition was individually filled into a transparent glass bottle (with a lid), and the presence or absence of precipitation was visually observed in the test samples immediately after preparation. The test samples were then allowed to stand in the dark at 5° C. for 2 days, and the presence or absence of precipitation after storage was visually observed.

Table 1 shows the results. FIG. 1 shows images of the appearance of the test samples taken immediately after preparation and after storage.

The above results show that further incorporating component (D) into a liquid or semi-solid composition comprising components (A), (B), (C), and (E) improves the storage stability under a low-temperature condition, and suppresses the formation of precipitates.

Example 6

Solution (pH 3.6)
A composition in the form of an aqueous solution having the following formulation in which precipitation under a low-temperature condition was suppressed was prepared.

| Formulation | |
|---|---|
| L-ascorbic acid 2-glucoside | 2.0 (mass %) |
| Disodium edetate | 0.1 |
| Dipotassium glycyrrhizinate | 0.5 |
| Heparinoid | 0.3 |
| 1,3-Butylene glycol | 8.0 |
| 1,2-Pentanediol | 5.0 |
| Glycerin | 3.0 |
| Phenoxyethanol | 0.4 |
| Citric acid | Appropriate amount |
| Sodium citrate | Appropriate amount |
| Purified water | Balance |
| Total amount | 100.0 mass % |

Example 7

Gel (pH 6.9)
A composition in the form of gel having the following formulation in which precipitation under a low-temperature condition was suppressed was prepared.

| Formulation | |
|---|---|
| L-ascorbic acid 2-glucoside | 2.0 |
| Disodium edetate | 0.1 |

TABLE 1

| | | Examples | | | | | Comparative Examples | | |
|---|---|---|---|---|---|---|---|---|---|
| | | 1 | 2 | 3 | 4 | 5 | 1 | 2 | 3 |
| (A) | L-ascorbic acid | 3 | — | — | — | — | 3 | — | — |
| | L-ascorbic acid 2-glucoside | — | 3 | 3 | 2 | 2 | — | 3 | 2 |
| (B) | Disodium edetate | 0.1 | 0.1 | 0.1 | 0.1 | 0.1 | 0.1 | 0.1 | 0.1 |
| (C) | Dipotassium glycyrrhizinate | 0.05 | 0.05 | 1 | 0.05 | 1 | 0.05 | 0.05 | 0.05 |
| (D) | Heparinoid | 0.3 | 0.3 | 0.1 | 0.3 | 0.1 | — | — | — |
| (E) | Purified water | Balance | Balance | Balance | Balance | Balance | Balance | Balance | Balance |
| | Total | 100 | 100 | 100 | 100 | 100 | 100 | 100 | 100 |
| Evaluation | Before storage (presence or absence of precipitation) | None | None | None | None | None | None | None | None |
| | After storage* (presence or absence of precipitation) | None | None | None | None | None | Slightly precipitated | Precipitated | Precipitated |
| | Stability evaluation | ○ | ○ | ○ | ○ | ○ | × | ×× | ×× |

*Evaluation after 2 days at 5° C.

-continued

| Formulation | |
|---|---|
| Dipotassium glycyrrhizinate | 0.05 |
| Heparinoid | 0.1 |
| Isopropyl methylphenol | 0.1 |
| Tocopherol acetate | 0.1 |
| 1,2-Pentanediol | 3.0 |
| 1,3-Butylene glycol | 5.0 |
| Carboxyvinyl polymer | 0.7 |
| Hydroxypropyl methylcellulose | 0.5 |
| Methylpolysiloxane | 2.6 |
| Anhydrous silicic acid | 0.5 |
| (Dimethicone/vinyl dimethicone) crosspolymer/dimethicone | 0.5 |
| Polysorbate 80* | 1.0 |
| Polyoxyethylene polyoxypropylene decyl tetradecyl ether | 0.5 |
| Methylparaben | 0.1 |
| Citric acid | Appropriate amount |
| Sodium citrate | Appropriate amount |
| Potassium hydroxide | Appropriate amount |
| Purified water | Balance |
| Total amount | 100.0 mass % |

*Polyoxyethylene sorbitan monooleate (20E.O.)

The invention claimed is:

1. A composition for external use, comprising the following components (A) to (E), based on the total amount of the composition taken as 100 mass %:
   (A) at least one member selected from the group consisting of ester derivatives of ascorbic acid, ether derivatives of ascorbic acid, and salts thereof, in a total amount of 0.3 to 10 mass %;
   (B) an edetic acid salt in an amount of 0.01 to 0.5 mass %;
   (C) a glycyrrhizic acid salt in an amount of 0.001 to 5 mass %;
   (D) a heparinoid; and
   (E) water;
   wherein
      the component (D) is present in a total amount of 3 to 20 parts by mass relative to 100 parts by mass of the component (A),
      the component (D) is present in a total amount of 50 to 500 parts by mass relative to 100 parts by mass of the component (B), and
      the component (D) is present in a total amount of 10 to 1000 parts by mass relative to 100 parts by mass of the component (C).

2. The composition for external use according to claim 1, which is a pharmaceutical product or a quasi-drug.

3. The composition for external use according to claim 1, wherein the amount of the component (D) is 0.01 to 1 mass % based on the total amount of the composition taken as 100 mass %.

4. The composition for external use according to claim 1, which comprises the following amount of the components (A) to (D), based on the total amount of the composition taken as 100 mass %:
   the component (A) in a total amount of 1 to 5 mass %;
   the component (B) in an amount of 0.05 to 0.2 mass %;
   the component (C) in an amount of 0.05 to 2 mass %; and/or
   the component (D) in an amount of 0.05 to 0.4 mass %.

* * * * *